US00RE46442E

(19) United States
(12) Reissued Patent
Bencteux et al.

(10) Patent Number: US RE46,442 E
(45) Date of Reissued Patent: Jun. 20, 2017

(54) CATHETER WINDER/UNWINDER AND AN ARTERIOGRAPHY SYSTEM PROVIDED WITH SUCH A WINDER/UNWINDER

(71) Applicant: Philippe Bencteux, Bois-Guillaume (FR)

(72) Inventors: Philippe Bencteux, Bois-Guillaume (FR); Steevy Cordette, Orsay (FR)

(73) Assignee: Philippe Bencteux, Bois-Guillaume (FR)

(21) Appl. No.: 13/861,854

(22) Filed: Apr. 12, 2013

Related U.S. Patent Documents

Reissue of:
(64) Patent No.: 7,927,310
Issued: Apr. 19, 2011
Appl. No.: 11/563,854
Filed: Nov. 28, 2006

(30) Foreign Application Priority Data

Nov. 30, 2005 (FR) ..... 05 12166

(51) Int. Cl.
*A61M 5/178* (2006.01)
*A61B 1/00* (2006.01)
*A61M 25/00* (2006.01)
*A61M 25/01* (2006.01)

(52) U.S. Cl.
CPC ..... *A61M 25/002* (2013.01); *A61M 25/0113* (2013.01)

(58) Field of Classification Search
CPC ..... A61B 19/026; A61B 19/0287; A61B 19/0274; A61B 19/0278; A61B 19/0279; A61B 19/2211
USPC ..... 604/500, 510, 523, 528, 165.02, 165.04, 604/158–159, 95.01, 271–272; 600/102, 600/106, 114, 137, 117–118
See application file for complete search history.

(56) References Cited

U.S. PATENT DOCUMENTS

| | | | | |
|---|---|---|---|---|
| 6,171,234 | B1 * | 1/2001 | White et al. | 600/102 |
| 6,358,199 | B1 * | 3/2002 | Pauker et al. | 600/114 |
| 6,485,482 | B1 * | 11/2002 | Belef | 604/528 |
| 6,726,675 | B1 * | 4/2004 | Beyar | 604/510 |

(Continued)

FOREIGN PATENT DOCUMENTS

| | | |
|---|---|---|
| EP | 0 471 547 A1 | 2/1992 |
| EP | 0 970 663 A1 | 1/2000 |

(Continued)

OTHER PUBLICATIONS

European Search Report and Written Opinion EP 06 29 1808; report dated Mar. 7, 2007.

(Continued)

*Primary Examiner* — Catherine S Williams
(74) *Attorney, Agent, or Firm* — Miller, Matthias & Hull LLP

(57) ABSTRACT

A catheter winder/unwinder comprising at least a first system and a second system is disclosed wherein, the first system comprises a first receptacle that receives a catheter and a first drive mechanism that applies movement to the catheter, the second system comprising a second receptacle that receives a guide and including an outlet, said second receptacle being rotatable relative to the first receptacle, and a second drive mechanism that applies movement to the guide. The outlet includes a fastener device for fastening to the catheter.

26 Claims, 8 Drawing Sheets

(56) References Cited

U.S. PATENT DOCUMENTS

| | | | | |
|---|---|---|---|---|
| 2001/0011164 | A1 | 8/2001 | Bierman | |
| 2002/0038116 | A1 | 3/2002 | Lee et al. | |
| 2002/0095175 | A1 | 7/2002 | Brock et al. | |
| 2002/0177789 | A1 | 11/2002 | Ferry et al. | |
| 2003/0176770 | A1* | 9/2003 | Merril et al. | 600/118 |

FOREIGN PATENT DOCUMENTS

| | | | |
|---|---|---|---|
| EP | 1 442 720 | A1 | 8/2004 |
| WO | WO 99/45994 | | 9/1999 |
| WO | WO 00/33723 | | 6/2000 |
| WO | WO 2005/000105 | A2 | 1/2005 |

OTHER PUBLICATIONS

Ernst et al., "Initial Experience with Remote Catheter Ablation Using a Novel Magnetic Navigation System," *Circulation*, vol. 109, pp. 1472-1475, (2004).

Beyar et al., "Remote-Control Percutaneous Coronary Interventions," Journal of the American College of Cardiology, vol. 47, No. 2 pp. 296-300. (2006).

* cited by examiner

CATHETER WINDER/UNWINDER AND AN ARTERIOGRAPHY SYSTEM PROVIDED WITH SUCH A WINDER/UNWINDER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present invention relates to catheter winders/unwinders and to arteriography systems provided with such winders/unwinders.

FIELD OF THE INVENTION

Manual introduction of catheters or guides into the inside of the body of a patient, performed by a practitioner, e g in order to perform an arteriography, is unsatisfactory since it is generally carried out under X-rays in order to allow the practitioner to view the displacement of the end of the catheter inside the patient's body while it is being inserted This results in the practitioner being irradiated, and although not more harmful per se than the patient being irradiated, this constitutes a difficulty since the practitioner is liable to repeat the operation on numerous patients, thus leading to exposure to considerable doses of X-rays.

Consequently, it would be desirable to have means for automating and remotely controlling such arteriography via a controller; thereby enabling the practitioner to guide the insertion of the catheter into the patient's body remotely.

BACKGROUND OF THE INVENTION

Document WO 2005/000105 describes numerous examples of such controllers Nevertheless, a problem remains with all of those embodiments. During insertion, the portions of the various catheters or guides that have not yet been inserted need to be kept in a suitable liquid medium to prevent them from becoming contaminated by external elements, and that is not made possible by any of the embodiments described in that document

SUMMARY OF THE INVENTION

To this end, the invention provides a catheter winder/unwinder comprising at least a first system and a second system, the first system comprising:

a first receptacle adapted to receive a first elongate tubular hollow member for inserting into a duct of a patient and extending between a first end and a second end along a longitudinal direction of the first member;

said first receptacle including an opening formed to allow said first member to pass towards the outside of the first system;

a first drive mechanism adapted to apply movement to the first member through said opening relative to said first receptacle;

the second system comprising:

a second receptacle adapted to receive a second elongate tubular member for inserting into the duct and extending between a first end and a second end along a longitudinal direction of the second member;

said second receptacle having an outlet formed to allow the second member to pass to the outside of the second system and towards the inside of the first system;

said second receptacle being mounted to rotate relative to the first receptacle about an axis of rotation;

a second drive mechanism adapted to apply to the second member at least movement along said longitudinal direction of the second member relative to said second receptacle;

said outlet including a fastener device for fastening to the first member and adapted to enable the first member and the second receptacle to move together along the longitudinal direction of the first member.

By means of these dispositions, a catheter winder/unwinder is obtained that is in the form of receptacles capable of containing both the preservation liquid and the catheters in question Furthermore, the assembly is made in a manner that is compact and that can be provided in the form of consumables. Construction around a single axis of rotation also makes a modular arrangement possible, thus making it easy to use two or more catheters during an operation, as is often required in practice, without it being necessary to make provision for numerous manipulations of the mechanism during the insertion operation.

In preferred embodiments of the invention, recourse may optionally be had to one or more of the following dispositions:

the first receptacle presents a bottom adapted to receive said first elongate member, and at least a first guide surface;

the second receptacle presents a bottom adapted to receive said elongate guide, and at least one second guide surface co-operating with said first guide surface of the first receptacle to guide relative movement of the first and second receptacles about said axis of rotation;

the first drive mechanism is adapted to apply to the first member at least one of the following kinds of movement relative to said first receptacle:

movement in translation along said longitudinal direction of the first member; and movement in rotation about said longitudinal direction of the first member;

the second drive mechanism is adapted to apply to the second member relative to said second receptacle at least one of the following kinds of movement:

movement in translation along said longitudinal direction of the second member, and movement in rotation about said longitudinal direction of the second member;

a motor mechanism is adapted to impart relative movement of the first and second receptacles about said axis of rotation;

the catheter winder/unwinder further comprises, as its first member, an elongate catheter extending in the first receptacle between a first end and a second end along a longitudinal direction of the first member, said second end being fastened to said fastener device, the elongate catheter co-operating with said first drive mechanism so that it imparts movement thereto relative to said first receptacle;

the catheter winder/unwinder further comprises, as its second member, an elongate guide extending in the second receptacle between a first end and a second end along a longitudinal direction of the second member, the elongate guide co-operating with said second drive mechanism so that it imparts movement thereto relative to said second receptacle, said first end of the guide passing through said outlet to the inside of the catheter;

the receptacles contain a liquid suitable for preserving members for insetting in a duct in a patient;

said drive mechanisms are made to be removable relative to their respective systems;

the second receptacle is adapted also to receive a third elongate tubular member for insertion into the duct and extending between a first end and a second end along a longitudinal direction of the third member, the second system including a third drive mechanism adapted to apply to the third member at least movement along said longitudinal direction of the third member relative to said second receptacle without applying movement to the second member, the second drive mechanism being adapted to apply to the second member said movement along the longitudinal direction of the second member without applying movement to the third member;

the catheter winder/unwinder further comprises a third system comprising:

a third receptacle adapted to receive a third elongate tubular member for insetting in the duct and extending between a first end and a second end along a longitudinal direction of the third member, said third receptacle including an outlet formed to allow the third member to pass therethrough, said third receptacle being mounted to rotate relative to the second receptacle about said axis of rotation, a third drive mechanism adapted to apply to the third member at least movement through said outlet of the third receptacle along said longitudinal direction of the third member relative to said third receptacle, the outlet of the third receptacle including a fastener device for fastening to the second member and adapted for the second member and the third receptacle to move together along the longitudinal direction of the second member;

the catheter winder/unwinder further comprises a third system comprising:

a third receptacle adapted to receive a third elongate tubular member for inserting in the duct and extending between a first end and a second end along a longitudinal direction of the third member, said third receptacle including an outlet formed to allow the third member to pass therethrough, said third receptacle being mounted to rotate relative to the second receptacle about said axis of rotation, a third drive mechanism adapted to apply to the third member at least movement through said outlet of the third receptacle along said longitudinal direction of the third member relative to said third receptacle, the outlet of the third receptacle including a fastener device for fastening to the first member and adapted to enable the first member and the third receptacle to move together along the longitudinal direction of the first member;

at least one drive mechanism comprises an electric motoring device having at least one electric motor adapted, on being powered electrically, to generate relative movement of the receptacle and a corresponding element to be moved selected amongst said members;

said drive mechanism comprises an equipment mounted to move relative to the receptacle in a first degree of freedom, said element to be moved is mounted to move on said equipment in a second degree of freedom distinct from the first degree of freedom, said electric motoring device is adapted to generate relative movement of the equipment and the receptacle in the first degree of freedom in order to generate degree of freedom, said electric motoring device being adapted to generate relative movement of the equipment and the element to be moved in the second degree of freedom so as to generate relative movement of the element to be moved and the receptacle in said second degree of freedom;

said electric motoring device comprising at least one electric motor, said electric motors being disposed on the receptacle and not on the equipment, said electric motor device including at least one movement transfer element connected to one of said electric motors for transmitting said relative movement of the element to be moved and the equipment in the second degree of freedom from said electric motor;

each receptacle is in the form of a tank

In another aspect, the invention provides an arteriography system including such a catheter winder/unwinder In an embodiment, the arteriography system further includes a central unit adapted to control the drive mechanisms In another aspect, the invention provides an installation including a catheter winder/unwinder comprising a receptacle adapted to receive an elongate tubular member for insertion into a duct of a patient and extending between a first end and a second end along a longitudinal direction;

the receptacle having an opening formed to allow said member to pass to the outside;

the winder/unwinder further comprising a drive mechanism adapted to apply to the member movement through said opening relative to said receptacle, said drive mechanism comprising:

an equipment mounted to move relative to the receptacle in a first degree of freedom, the equipment carrying the member; and an electric motoring device adapted to generate movement when powered electrically;

said electric motoring device being adapted to generate relative movement between the equipment and the receptacle in the first degree of freedom so as to generate relative movement of the member and of the receptacle in said first degree of freedom;

the member being mounted to move relative to the equipment in a second degree of freedom distinct from the first degree of freedom;

said electric motoring device being adapted to generate relative movement of the equipment and of the member in the second degree of freedom in order to generate relative movement of the member and of the receptacle in said second degree of freedom;

said electric motoring device comprising at least an electric motor, said electric motoring device comprising at least one movement transfer element connected to one of said electric motors to transmit said relative movement of the member and the equipment in the second degree of freedom from said electric motor;

the installation comprising a permanent portion comprising said electric motors, and a utilized replaceable portion, distinct from said member, mounted removably relative to the permanent portion, the permanent portion and the replaceable portion in an assembled state together forming said winder/unwinder, the installation having a plurality of replaceable replacement portions that are identical to the utilized replacement portion.

Such an installation makes it possible to use a replaceable portion as a consumable, thus making it possible to guarantee the hygiene conditions required for such an installation while minimizing costs, since only the consumable portion is replaced between two utilizations.

In preferred embodiments of this installation, recourse may also be had to one or more of the following dispositions:

the replaceable portion comprises at least the receptacle;

the permanent portion includes the entire drive mechanism; and the drive mechanism includes an application portion in contact with the member and adapted, in the assembled state, to be connected to the movement transfer mechanism to apply said relative movement of the member and of the receptacle in said second degree of freedom, and the replaceable portion comprises at least said application portion.

The electric motors positioned on the receptacle but not on the moving equipment make it possible to provide the moving equipment as a consumable, without it being necessary to replace the electric motors after each operation, given that the motors are amongst the most expensive elements of the system In another aspect, the invention provides a catheter winder/unwinder comprising a base adapted to receive a tubular member for inserting into a duct of a patient and extending between a first end and a second end along a longitudinal direction of the member, and a drive mechanism adapted to apply to said tubular member at least movement along said longitudinal direction, said drive mechanism comprising:

a plate adapted to carry the member and mounted to rotate relative to the base about said longitudinal direction;

an application portion mounted to move on the plate, in contact with the member;

a worm screw mounted on the plate and adapted to drive said application portion; and an electric motoring device adapted to drive the worm screw.

A winder/unwinder of such a construction is relatively simple and inexpensive to make, while also being robust and very easy to use

BRIEF DESCRIPTION OF THE DRAWINGS

Other characteristics and advantages of the invention appear from the following description of five embodiments, given by way of non-limiting example, and with reference to the accompanying drawings.

In the drawings:

FIG. 10 is a fragmentary plan view of a fifth embodiment of the invention In the various figures, the same references are used to designate elements that are identical or similar

MORE DETAILED DESCRIPTION

Figure 1:
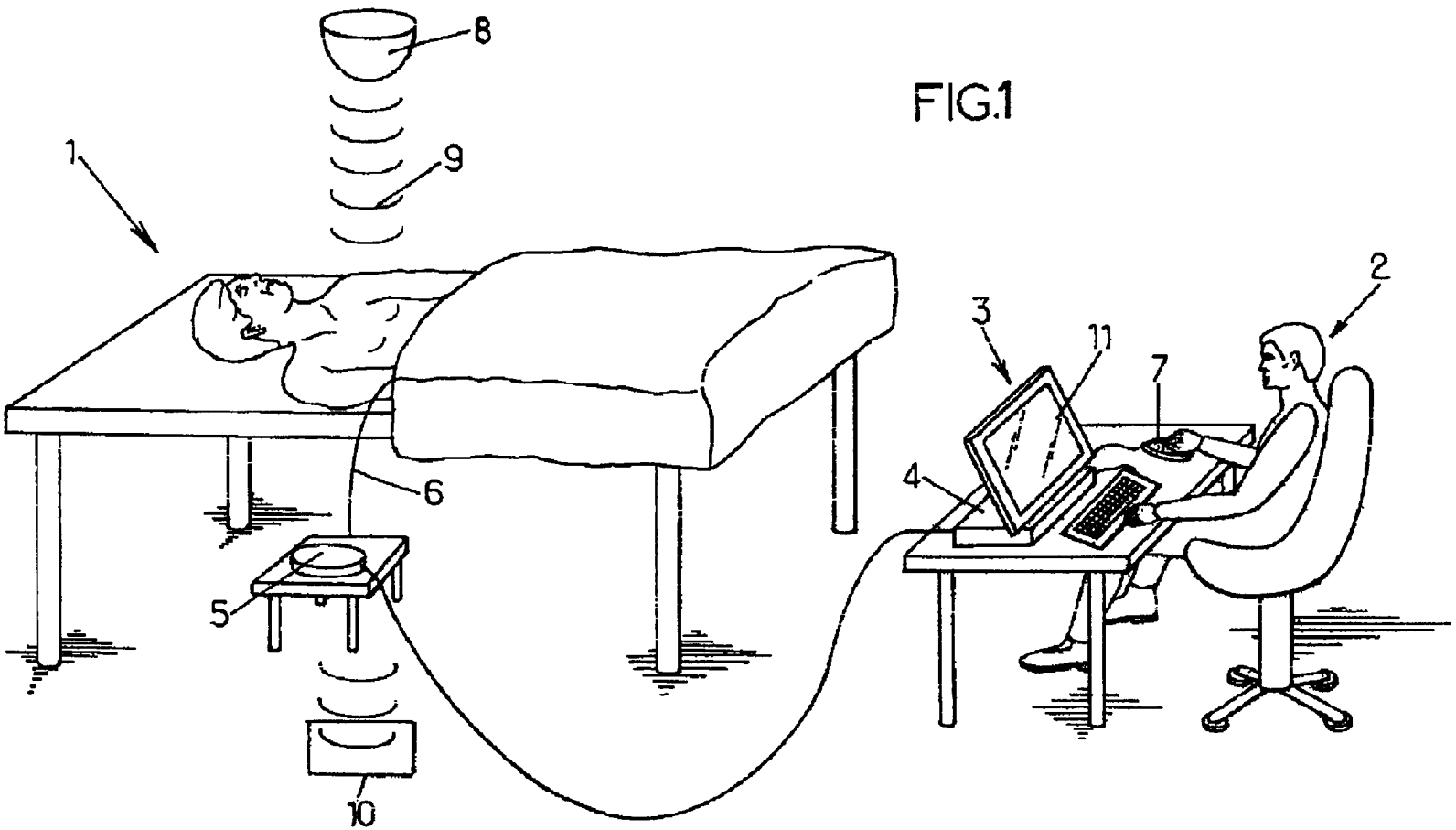
FIG. 1 is a diagrammatic perspective view of an arteriography system.

In FIG. 1, a patient 1 is being subjected to arteriography The arteriography is carried out by trained personnel 2, e g such as a surgeon or qualified medical personnel, using an automatic arteriography system 3 including, for example, a programmable machine 4 remotely controlling a catheter winder/unwinder 5 disposed close to the patient 1.

The displacement of a catheter 6 within the body of the patient 1 is remotely controlled by the qualified personnel 2 using control means 7, such as a mouse, for example, connected to the programmable machine 4

The installation further comprises an X-ray source 8 emitting X-rays 9 towards the patient 1, and an X-ray detector 10 suitable for detecting the radiation passing through the patient 1. The detector 10 may be connected to the computer 4 in order to display a detected image on the computer screen 11.

Figure 2:
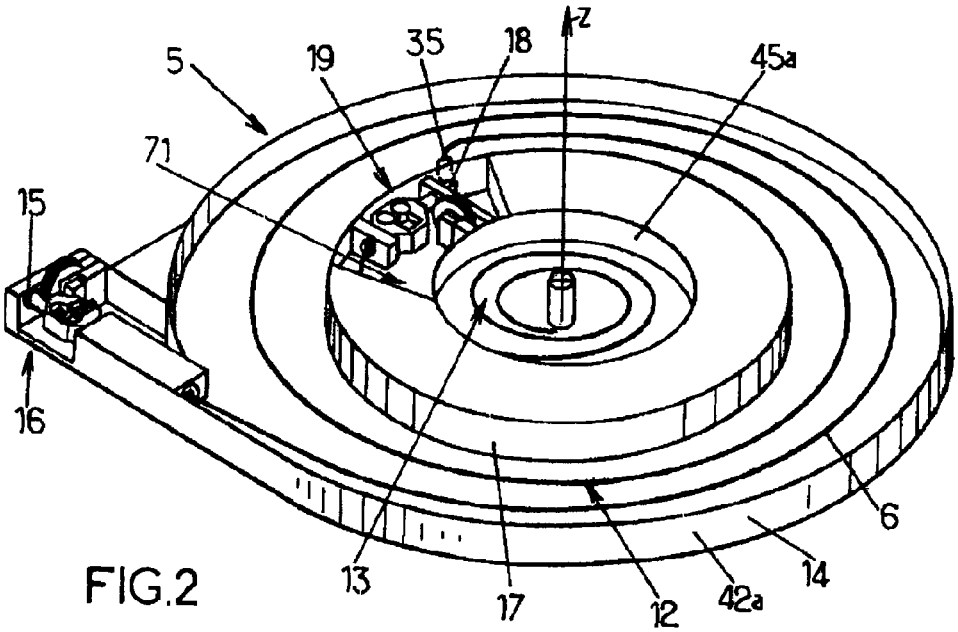
FIG. 2 is a diagrammatic perspective view of an embodiment of a catheter winder/unwinder.

As shown in FIG. 2, the winder/unwinder 5 comprises at least a first system 12 and a second system 13 that are concentric and disposed about an axis Z, e.g. extending vertically.

The first system 12 comprises a first receptacle 14 in the form of a hollow tank or trough having an outer wall 42a and an inner wall 42b that are substantially vertical defining between them a bottom wall on which there is placed, prior to use, a tubular catheter that is to be inserted into an artery of the patient 1. The catheter extends from a first end to a second end along a catheter longitudinal direction The trough 14 is also filled with a preservation liquid in which the catheter is immersed. The first receptacle 14 has an opening 15 through which the catheter can reach the outside 12, and in particular the inside of the body of the patient 1. The first system 12 also includes a drive mechanism 16 that is described in greater detail below with reference to FIGS. 3a and 3b. By way of example, the drive mechanism is situated upstream from the opening 15 in the longitudinal direction of the catheter, and is controlled by the surgeon 2 by means of the computer 4.

The second system 13 comprises a second receptacle 17 capable of turning about the axis Z relative to the first receptacle 14. In this respect, provision can be made for the second receptacle 17 to present a central opening 45b that co-operates with the inner wall 42b of the first receptacle. The second receptacle 17 also has an outlet 18 via which a guide 37 contained in the second receptacle 17 can access the outside of the second receptacle, and in particular the inside of the first receptacle 14.

The second receptacle 17 comprises a trough or tank having a cylindrical outer wall 45a, and it receives a tubular guide extending between first and second ends along a guide longitudinal direction, and immersed in a liquid suitable for preserving it. Furthermore, the second receptacle 17 also includes a drive mechanism 19 similar to the first drive mechanism 16 of the first system 12, located outside the trough and described in greater detail below with reference to FIGS. 3a and 3b.

Figure 3A:
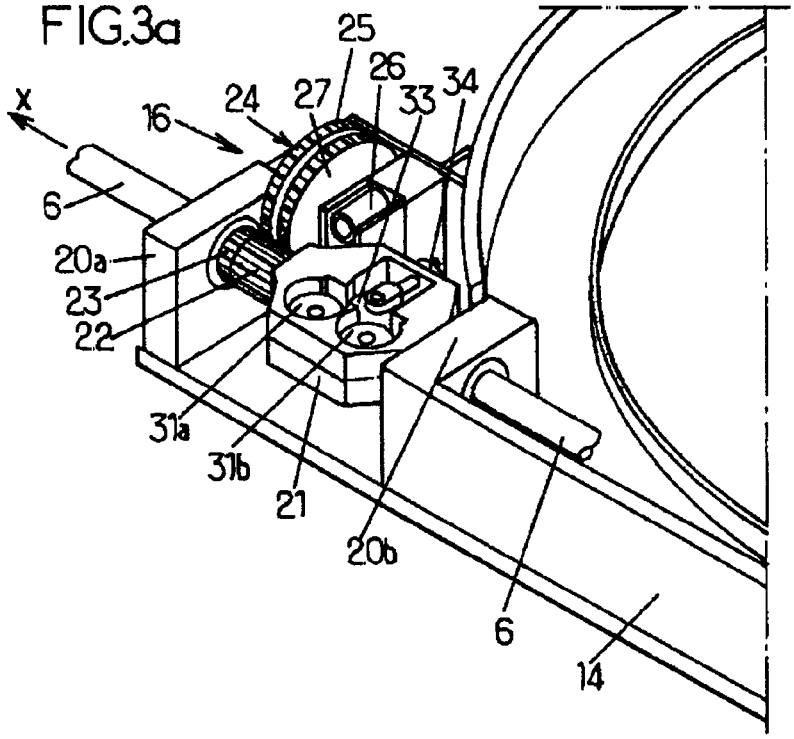
FIG. 3a is a perspective view from above of a drive mechanism for the FIG. 2 winder/unwinder.

FIG. 3a shows the first drive mechanism 16 in an illustrative embodiment. The second drive mechanism 19 can be made in similar manner. The first drive mechanism 16 comprises a moving equipment mounted to rotate relative to the first receptacle 14 about the longitudinal axis X of the catheter 6 in two bearings 20a and 20b of the first receptacle. In the example described, the moving equipment comprises a plate 21 described in greater detail below carrying the catheter, and a cylindrical rotation ring gear 23 mounted on a cylindrical shaft 49, with the catheter 6 passing inside them.

The first drive mechanism 16 includes a rotation electric motor 24 (not visible in FIG. 3a) serving, when powered with electricity under control of the computer 4, to rotate a rotation gear 25 that co-operates with the rotation ring gear 23 of the moving equipment.

The drive mechanism 16 also includes a translation electric motor 26 which serves, when powered electrically under the control of the computer 4, to rotate a translation gear 27 that co-operates with a translation ring gear 22 mounted to rotate freely on the cylindrical shaft 49 secured to the rotation ring gear 23 and through which the catheter 6 passes.

In a variant, provision could be made to use a single motor coupled either to one or to the other of the rotation gear 25 and the translation gear 27 By way of example, these motors may be stepper motors.

Figure 3B:
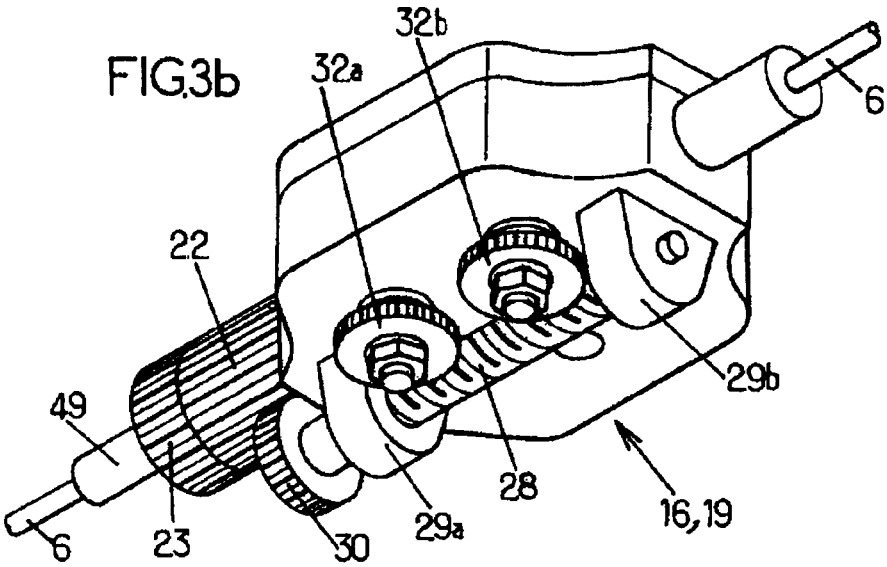
FIG. 3b is a perspective view from below of the FIG. 3a drive mechanism.

As shown in FIG. 3b, the translation ring gear 22 rotates a worm screw 28 mounted to rotate in two beatings 29a and 29b, and receiving drive via an intermediate gear 30. The rotation about an axis parallel to the axis X of the worm screw 28 drives rotation about the axis Z of two drive wheels 31a and 31b disposed on the top face of the plate (FIG. 3a), with drive passing via two corresponding gear wheels 32a and 32b.

The catheter 6 is kept in contact with the edge of each of the drive wheels 31 by a non-motor-driven bias wheel 33 whose position relative to the plate is defined by an adjustment mechanism 34 serving to adapt the presently-described drive mechanism 16 to catheters of different diameters With the catheter being held in engagement with the drive wheels 31a and 31b by the bias wheel 33, rotation of the drive wheels entrains displacement of the catheter along its longitudinal axis X These drive wheels 31a, 31b thus for an application portion, applying movement to the catheter.

Figure 4:
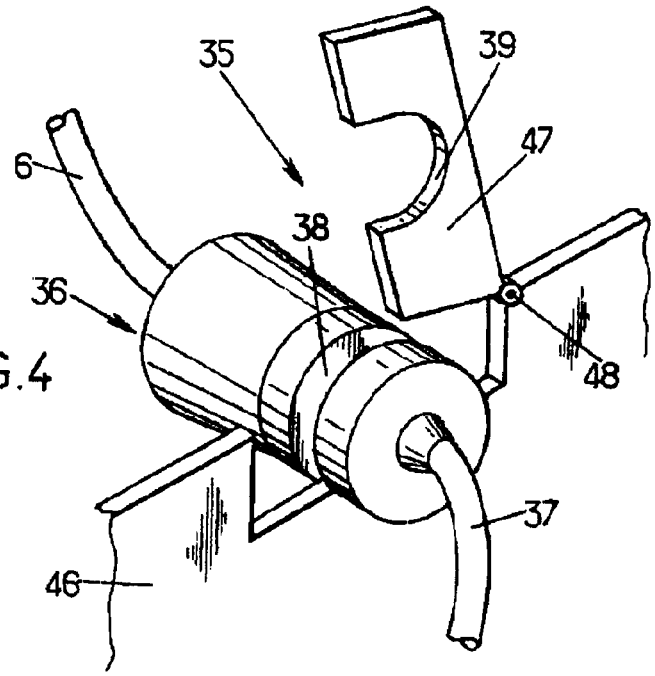
FIG. 4 is a detailed fragmentary perspective view of an embodiment of a fastener device.

As shown in FIG. 2, and in greater detail in FIG. 4, the outlet 18 from the second receptacle 17 includes a fastener device 35 allowing the catheter 6 to rotate freely about its longitudinal axis relative to the second receptacle 17, and allowing the second receptacle 17 to be driven when the catheter 6 is driven in translation in its longitudinal direction. In a purely illustrative example of the fastener device 35 as shown in FIG. 4, the distal end of the catheter 6 is secured to a ring 36 having a groove 38 that is inserted in a complementary orifice 39 formed in the wall 46 of the second receptacle. Half of this orifice 39 is formed in the wall 46, while its other half is formed in a flap 47 pivoting on a hinge 48 on the wall 46, for example FIG. 4 shows the flap 47 in the open position for insertion of the ring 36 in the orifice 39. The ring 36 is thus free to rotate relative to the wall 46 of the first receptacle 17 about a longitudinal axis Y of the guide 37. The ring may present a shape that flares towards the catheter 6 in order to make it easier to grip by a user In a variant, the flap could be replaced by an opening fitted on the wall.

It should be observed that the embodiment shown in FIG. 2 could be made in modular manner, for example, i.e. the first system 12 and the second system 13 could be sold separately and assembled together depending on the requirements for examining the patient.

Figure 5:
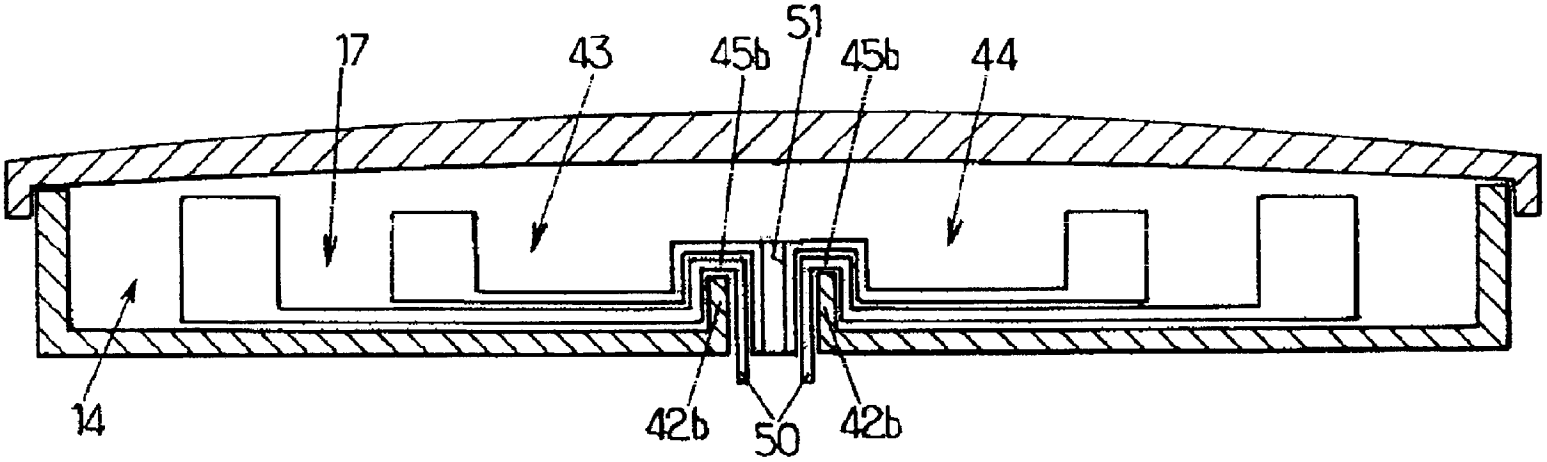
FIG. 5 is a detailed section view of a second embodiment.

It is also possible to provide a third system 43 that is insertable in the second system and that is concentric therewith about the axis Z, to enable an intervention catheter to be inserted into the patient in addition to the guide and the catheter as shown in FIG. 5 In similar manner; the third system comprises a receptacle 44 in the form of a trough or tank suitable for containing a liquid, a drive mechanism, and an outlet opening out into the second system. The systems are disposed in such a manner that the element for insertion that presents the largest diameter (generally the catheter) is placed in the outermost system, and the element for insertion that presents the smallest diameter (generally the guide) is placed in the innermost system, in which configuration the intervention catheter will be placed in the intermediate system.

Furthermore, each system can itself be made in modular manner, i.e. the electric motors may be removed from the remainder of the system so as to be installed on a winder/unwinder having no electric motor, and that is itself put on the market as a consumable This greatly reduces costs associated with reusing the system, since the more expensive elements can be retained from one use to another (possibly being sterilized or decontaminated before subsequent reuse).

An example of using the device shown in FIGS. 1 and 2 is described below. A surgeon punctures an artery, e.g. the femoral artery in the groin, and puts into place a short pipe including a valve that provides access between the outside and the artery, and commonly known as a Desilet-Hoffman catheter introducer. The winder/unwinder of FIG. 2 is placed close to the patient and is connected to the computer 4. The winder/unwinder 5 already contains a preservative liquid in which there are immersed, in the first system a catheter, and in the second system a guide suitable for insertion in the catheter. By declutching the wheel 33 of the first system, the catheter can be moved so as to be inserted manually by the surgeon through the introducer into the artery. Thereafter, from the computer 4, the surgeon controls the translation electric motor of the second system to guide the guide 37 through the outlet 18 into the catheter 6 until the first end of the guide penetrates into the patient at the first end of the catheter. During this operation, the X-ray source 8 can emit radiation that has no effect on the surgeon 2, and the image picked up by the detector 10 can be displayed on the computer screen 11.

In order to enable the end of the catheter to reach the location of interest inside the body of the patient 1, the surgeon 2 controls the following functions from the computer 4:

- movement in translation of the guide: by activating the translation electric motor 26 of the second system, thereby rotating the translation ring gear 22, the intermediate gear 30, the wormscrew 28, the gear wheels 32a and 32b, and thus the drive wheels 31a and 31b which imparts movement in translation to the guide along its longitudinal direction inside the catheter 6;
- movement in rotation of the guide about the longitudinal axis of the guide by causing the rotation electric motor 24 to be actuated in the second system, thereby actuating the rotation gear 25 and the rotation ring gear 23 which rotates the entire moving equipment and the guide relative to the bearings 20a and 20b of the second system, and thus rotating the guide held on the equipment by the drive wheels 31 a, 31b and the bias wheel 33;

movement in translation of the catheter along its longitudinal direction under control similar to controlling movement in translation of the guide as described above (because the second end of the catheter is connected to the fastener device 35, this movement in translation causes the second system to turn freely about the axis Z relative to the first receptacle); and movement in rotation of the catheter, controlled in the same manner as described above for the guide, the fastener device 35 allowing the catheter 6 to turn about its longitudinal axis without influencing the guide 37 or the second receptacle 17.

In certain embodiments, provision can also be made to enable both the guide and the catheter to be controlled to move together in translation by controlling the two corresponding motors simultaneously.

Movement both in translation and in rotation can naturally be controlled in one direction or in the other for the purpose of moving the guide and the catheter to the site, or for the purpose of returning them.

The second receptacle can be caused to turn quickly relative to the first receptacle by driving the central opening 45b of the second receptacle in rotation by means of a specially-dedicated electric motor (not shown) connected under the bottom of the tank to the corresponding end 50 of said opening This dedicated motor can be used in particular for rewinding the guide after use.

As an alternative, the dedicated motor could be replaced for the rewinding function by a dedicated spring that is loaded by the movement of the receptacle under drive during deployment of the catheter which is connected to its opening.

Figure 6:
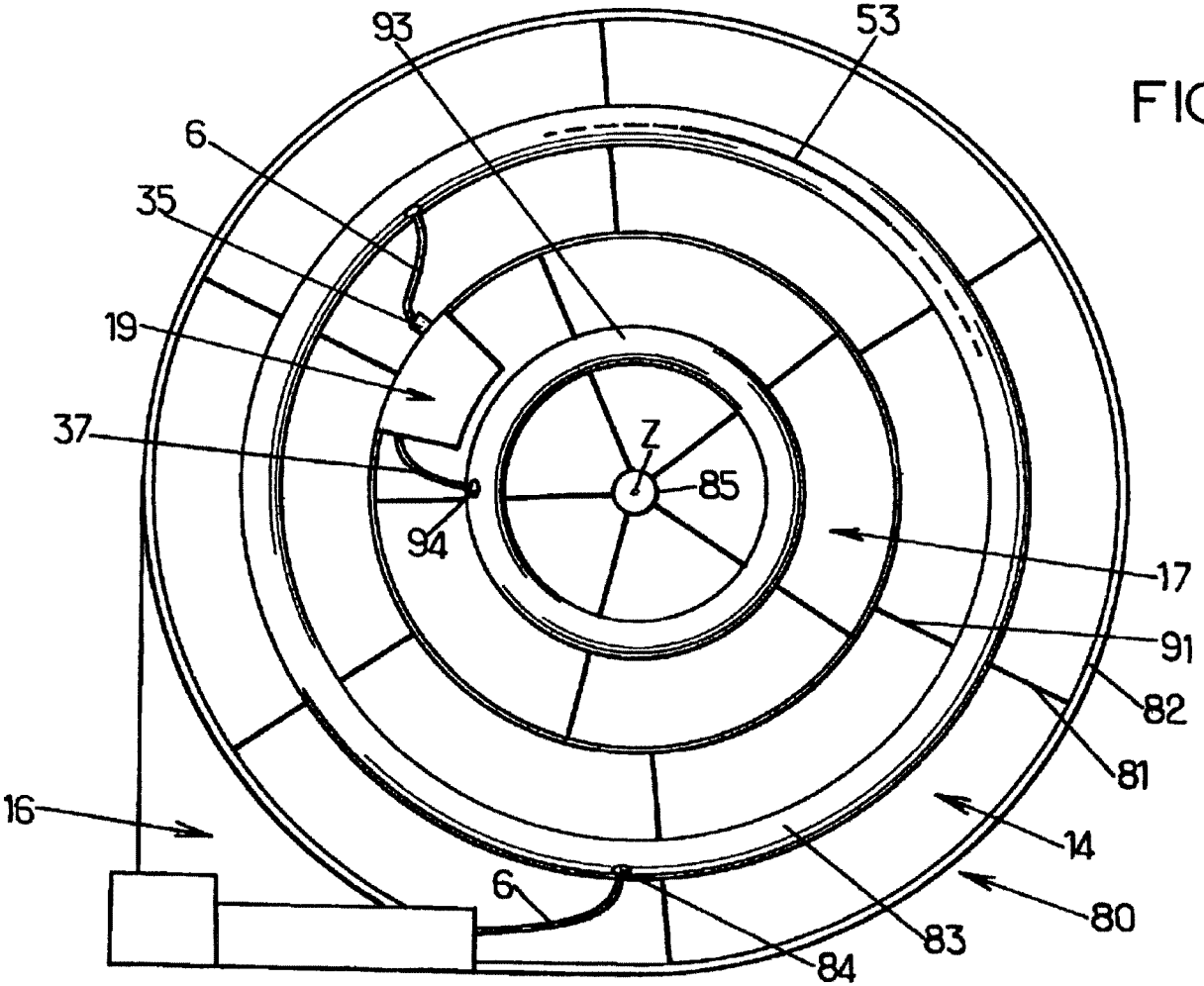
FIG. 6 is a diagrammatic view from above of a third embodiment.

As shown in FIG. 6, in a second embodiment, the receptacle of the first system is constituted by a first tray 80 having a plurality of spokes 81 extending from a central hub 85 to a peripheral edge 82. The tray 80 carries a first pipe 83 receiving the catheter 6 internally immersed in an appropriate preservation liquid. The first pipe 83 has an opening 84 through which the catheter exits towards the first drive mechanism 16 (not shown again) identical to that of FIG. 2.

The first tray 80 has placed thereon a second tray 90 similar to the first tray, and adapted to turn about the axis Z relative to the hub 85. The second tray 90 has spokes 91 extending to a peripheral edge 52 and carries a second pipe 93 receiving the guide 37 internally. This pipe has an opening 94 through which the guide exits going towards the second drive mechanism 19 (not shown again) The outlet 35 is made in the manner described above The guide 37 penetrates into the first pipe 83 via an elongate slot 53 therein, e.g. extending all the way round it (shown in part only). In operation, turning of the second tray 90 relative to the hub causes the second pipe 93 that is carried thereby to turn likewise.

In addition, in an embodiment that also includes inserting an intervention catheter, e.g. for the purpose of delivering a certain function to the site, the above-described operations and variants can also be implemented for the third system.

For this purpose, the end 51 of the third receptacle can also be driven by a dedicated electric motor (not shown) for rewinding the guide in a three-system winder/unwinder.

Figure 7:
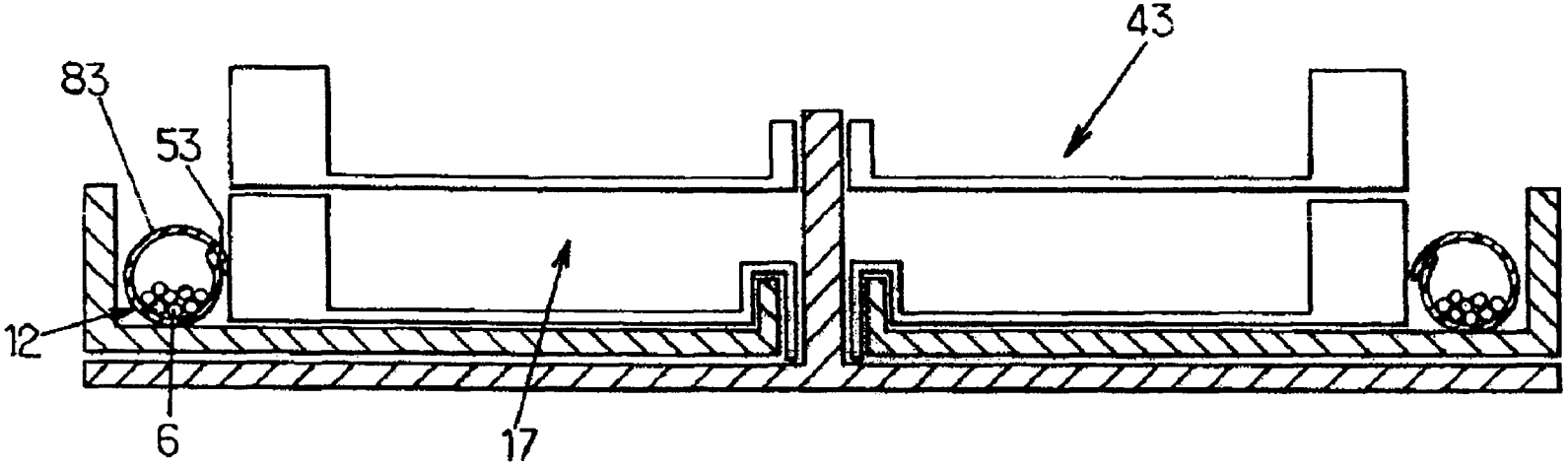
FIG. 7 is a detailed section view corresponding to FIG. 5 and showing a fourth embodiment.

FIG. 7 is a view corresponding to FIG. 5 for a third embodiment. In this embodiment, the third system 43 is superposed on the second system, rather than being contained therein Consequently, the outlet from the third system is no longer connected directly to the inlet of the second system, as in FIG. 5, but may be connected directly to the inlet of the first system. The connection of the second system or of the third system to the first system can take place in an alternative manner. For example, once the guide has been introduced into the body of the patient, and then the catheter along the guide, the guide can be withdrawn from the body of the patient, and the ring 36 taken away from the second receptacle and secured to the third receptacle containing the intervention catheter, for insertion into the body of the patient via the catheter In a variant, the second and third systems can be used in parallel for parallel, non-coaxial, insertion of both a guide and an intervention catheter, which are disposed respectively in the second and third receptacles. At the rear end of the catheter contained in the first receptacle, a T-shaped ring (not shown) can then be provided that includes a first inlet for connecting to the second receptacle with freedom to rotate, and a second inlet for connecting to the third receptacle, likewise with freedom to rotate.

As also shown in FIG. 7, the catheter 6 is placed in the leaktight pipe 83, e.g. made of plastics material, and that is adapted to also contain the catheter preservation liquid. This pipe 83 also presents the slot 53, e.g. made in the form of a thin lip for entry of the guide into the pipe.

The use of pipes is not limited to the embodiment of FIGS. 6 and 7, and can be envisaged for any other embodiment of the winder/unwinder.

Figure 10:
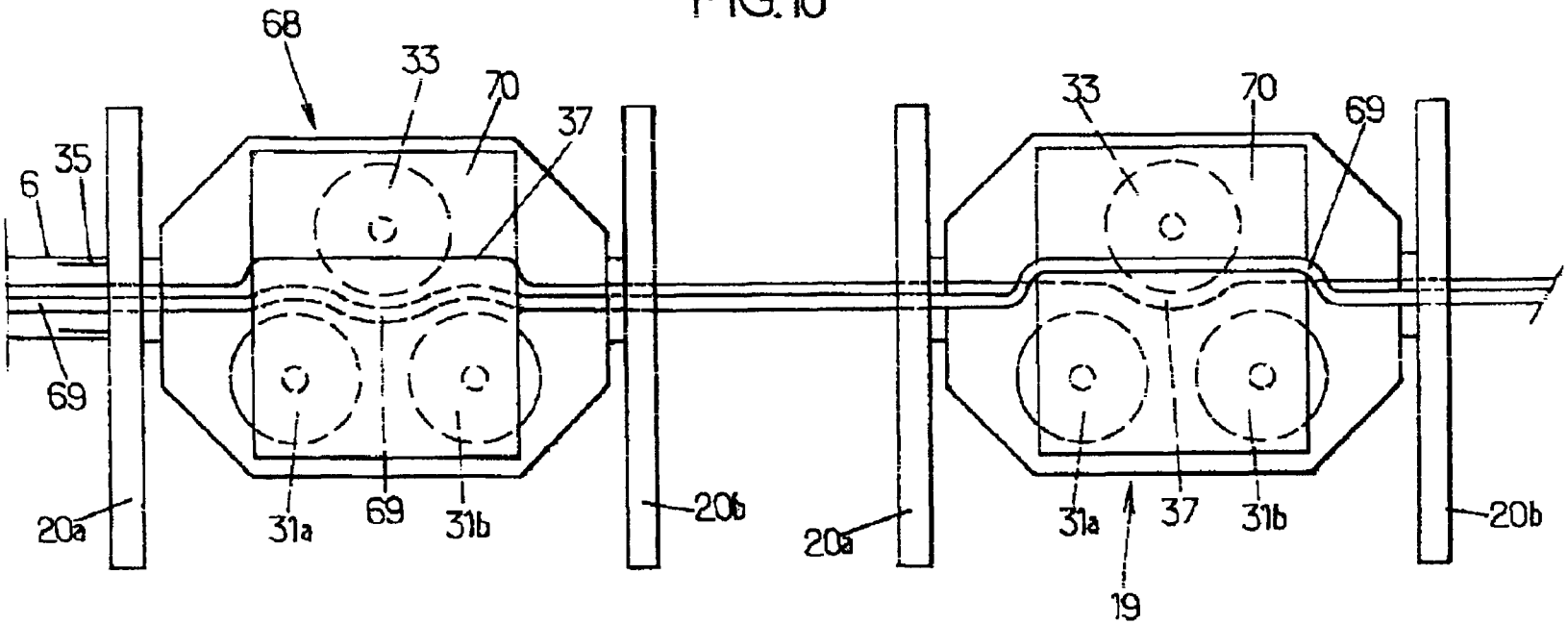

In a fifth embodiment, shown in FIG. 10, the guide 37 and the intervention catheter 69 are caused to pass in parallel in the catheter 6 while using only two receptacles.

This embodiment corresponds substantially to that of FIGS. 1 to 4 with the catheter 6 being secured to the second receptacle by the fastener device 35 Nevertheless, the second and third drive mechanisms 19 and 68 are disposed the one after the other in the location 71 (FIG. 2) provided for this purpose in the second system The guide and the intervention catheter are both placed in the second receptacle As shown in FIG. 10, the second drive mechanism 19 entrains the guide 37, while the intervention catheter 69 is held by a plate 70 apart from the wheels 31a, 31b, and 33. The guide and the intervention catheter pass together into the bearings 20a, 20b of the second drive mechanism. Similarly, the intervention catheter 69 is driven by the third drive mechanism 68, with the guide being held away by a plate 70. Both the guide and the intervention catheter pass together through the bearings 20a, 20b of the third drive mechanism. Thus, the second drive mechanism does not impart any movement to the intervention catheter, and the third drive mechanism does not impart any movement to the guide. Both the guide and the intervention catheter penetrate in parallel into the inside of the catheter 6. Where appropriate, the guide enters into the intervention catheter through a dedicated opening, downstream from the third drive mechanism.

Figure 8:
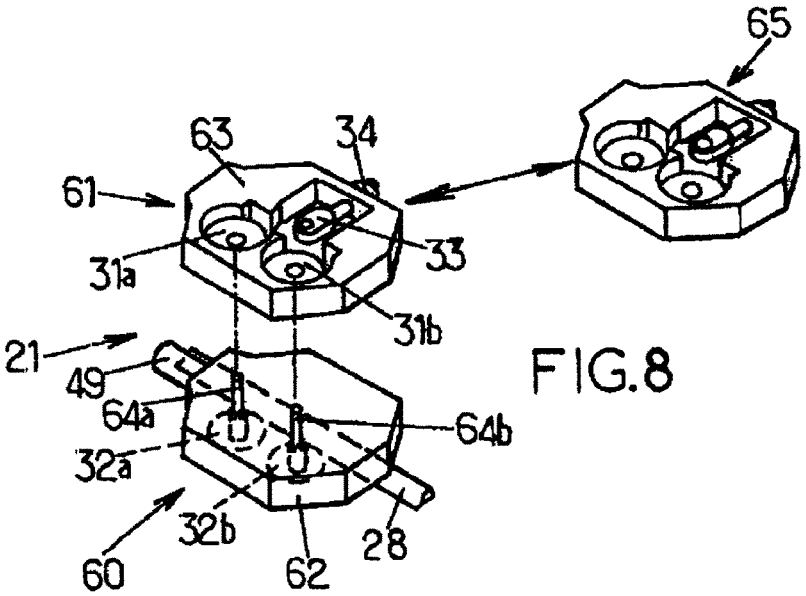
FIG. 8 is a fragmentary perspective view from above of an installation including the FIG. 3a drive mechanism, in a variant embodiment.

As shown in FIG. 8, the installation may comprise a permanent portion 60 and a replaceable portion 61 The replaceable portion 61 is a portion of the winder/unwinder itself and not the catheters or guides which are in any event conventionally exchanged after each operation By way of example, the replaceable portion comprises everything that becomes dirtied by coming into contact with the guides or the catheters or the liquid in which they are immersed while an operation is taking place. By way of example, the permanent portion may comprise the electric motors, which constitute portions of the winder/unwinder that are expensive and difficult to recycle. Two non-limiting embodiments are described below with reference to FIGS. 8 and 9.

In the embodiment of FIG. 8, the plate 21 is made up of two portions:

a bottom portion 62 carrying the wormscrew 28, the gear wheels 32, 32b, and the cylindrical shaft 49; and a top portion 63 carrying the wheels 31a, 31b, the bias wheel 33, and the adjustment mechanism 34.

In an assembled state, the replaceable portion formed by the top portion of the plate has its wheels 31a, 31b engaged on respective drive shafts 64a, 64b connected to the gear wheels.

After the winder/unwinder has been used for a first operation, the replaceable portion 61 used for this first operation can be removed from the permanent portion and can be replaced by a replacement portion 65 that is identical to the replaceable portion, in order to perform a subsequent operation.

In the embodiment of FIG. 8, the top portion 63 of the plate is made in the form of a replaceable portion that is removable relative to the permanent portion Alternatively, or in combination, other portions of the installation could be made to be replaceable.

Figure 9:
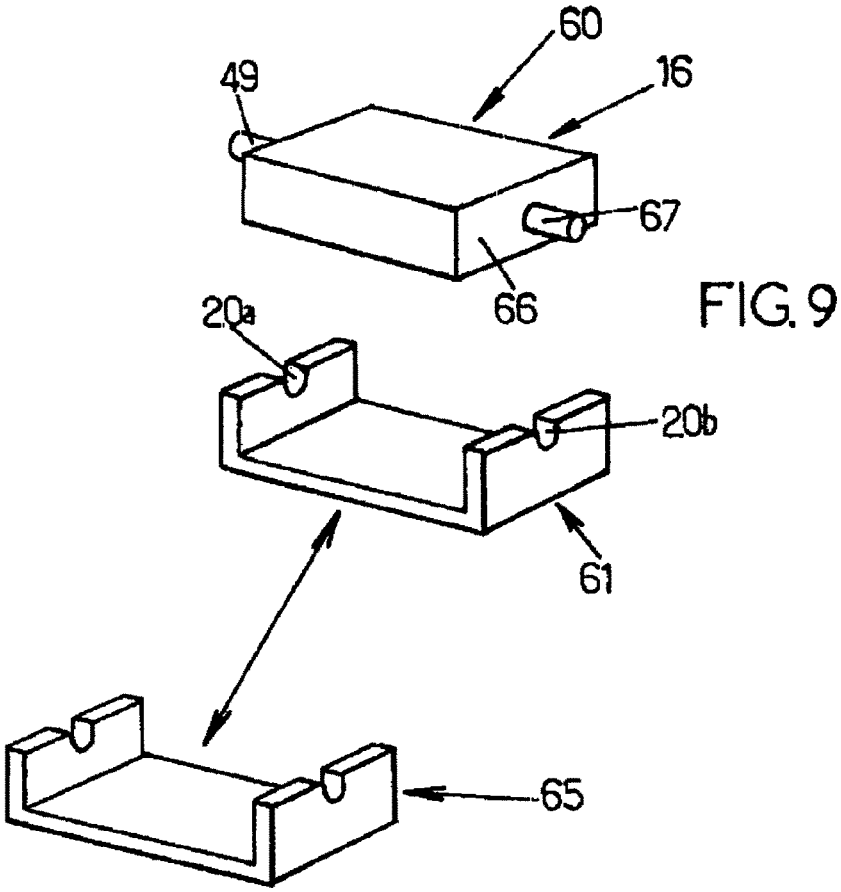
FIG. 9 is a fragmentary perspective view from above of an installation including the FIG. 3a drive mechanism, in another variant embodiment.

As shown in FIG. 9, the entire drive mechanism 16 is contained in a closed box 66 having the outlet shaft 49 and a similar shaft 67 as an inlet shaft. The box 66 forms the permanent portion 60 and the receptacle 14 forms the replaceable portion that is removably mounted relative to the permanent portion. Only the portion of the receptacle that is used for receiving the box is shown in FIG. 9. It comprises the two bearings 20a, 20b for receiving the shafts 49 and 67, respectively.

After the winder/unwinder has been used for a first operation, the replaceable portion 61 can be removed from the permanent portion, and can be replaced by a replacement portion 65 that is identical to the replaceable portion, in order to perform a subsequent operation. By way of example, the entire receptacle, possibly containing the member, can be replaced for each new operation.

The invention claimed is:

1. A catheter winder/unwinder comprising at least a first system and a second system, the first system comprising:

a first receptacle adapted to receive a first elongate tubular hollow member for inserting into a duct of a patient and extending between a first end and a second end along a longitudinal direction of the first member;

said first receptacle including an opening formed to allow said first member to pass towards the outside of the first system;

a first drive mechanism adapted to apply movement to the first member through said opening relative to said first receptacle;

the second system comprising:

a second receptacle adapted to receive a second elongate tubular member for inserting into the duct and extending between a first end and a second end along a longitudinal direction of the second member;

said second receptacle having an outlet formed to allow the second member to pass to the outside of the second system and towards the inside of the first system;

said second receptacle being mounted to rotate relative to the first [receptacle] *drive mechanism* about an axis of rotation;

a second drive mechanism adapted to apply to the second member at least movement along said longitudinal direction of the second member relative to said second receptacle;

said outlet including a fastener device for fastening to the first member and adapted to enable the first member and the second receptacle to move together along the longitudinal direction of the first member.

2. A catheter winder/unwinder according to claim 1, *wherein the second receptacle is mounted to rotate relative to the first receptacle about the axis of rotation,* wherein the first receptacle presents a bottom adapted to receive said first member, and at least a first guide surface;

wherein the second receptacle presents a bottom adapted to receive said elongate guide, and at least a second guide surface co-operating with said first guide surface of the first receptacle to guide the relative movement of the first and second receptacles about said axis of rotation.

3. A catheter winder/unwinder according to claim 1, wherein the first drive mechanism is adapted to apply to the first member at least one of the following kinds of movement relative to said first receptacle:

movement in translation along said longitudinal direction of the first member; and movement in rotation about said longitudinal direction of the first member.

4. A catheter winder/unwinder according to claim 1, wherein the second drive mechanism is adapted to apply to the second member relative to said second receptacle at least one of the following kinds of movement:

movement in translation along said longitudinal direction of the second member; and/or movement in rotation about said longitudinal direction of the second member.

5. A catheter winder/unwinder according to claim 1, further including a motor mechanism adapted to impart relative movement of the [first and] second [receptacles] *receptacle and the first drive mechanism* about said axis of rotation.

6. A catheter winder/unwinder according to claim 1, further including, as its first member, an elongate catheter extending in the first receptacle between a first end and a second end along a longitudinal direction of the first member, said second end being fastened to said fastener device, the elongate catheter co-operating with said first drive mechanism so that it imparts movement thereto relative to said first receptacle.

7. A catheter winder/unwinder according to claim 6, further including, as its second member, an elongate guide extending in the second receptacle between a first end and a second end along a longitudinal direction of the second member, the elongate guide co-operating with said second drive mechanism so that it imparts movement thereto relative to said second receptacle;

the first end of the guide passing through said outlet to the inside of the catheter.

8. A catheter winder/unwinder according to claim 1, wherein the receptacles contain a liquid suitable for preserving members for inserting in a duct in a patient.

9. A catheter winder/unwinder according to claim 1, wherein said drive mechanisms are made to be removable relative to their respective systems.

10. A catheter winder/unwinder according to claim 1, wherein the second receptacle is adapted also to receive a third elongate tubular member for insertion into the duct and extending between a first end and a second end along a longitudinal direction of the third member, the second system including a third drive mechanism adapted to apply to the third member at least movement along said longitudinal direction of the third member relative to said second receptacle without applying movement to the second member, the second drive mechanism being adapted to apply to the second member said movement along the longitudinal direction of the second member without applying movement to the third member.

11. A catheter winder/unwinder according to claim 1, further comprising a third system comprising:

a third receptacle adapted to receive a third elongate tubular member for inserting in the duct and extending between a first end and a second end along a longitudinal direction of the third member;

said third receptacle including an outlet formed to allow the third member to pass therethrough;

said third receptacle being mounted to rotate relative to the second receptacle about said axis of rotation;

a third drive mechanism adapted to apply to the third member at least movement through said outlet of the third receptacle along said longitudinal direction of the third member relative to said third receptacle;

the outlet of the third receptacle including a fastener device for fastening to the second member and adapted for the second member and the third receptacle to move together along the longitudinal direction of the second member.

12. A catheter winder/unwinder according to claim 1, further comprising a third system comprising:

a third receptacle adapted to receive a third elongate tubular member for inserting in the duct and extending between a first end and a second end along a longitudinal direction of the third member;

said third receptacle including an outlet formed to allow the third member to pass therethrough;

said third receptacle being mounted to rotate relative to the first receptacle about said axis of rotation;

a third drive mechanism adapted to apply to the third member at least movement through said outlet of the third receptacle along said longitudinal direction of the third member relative to said third receptacle;

the outlet of the third receptacle including a fastener device for fastening to the first member and adapted to enable the first member and the third receptacle to move together along the longitudinal direction of the first member.

13. A catheter winder/unwinder according to claim 1, wherein at least one drive mechanism comprises an electric motoring device having at least one electric motor adapted, on being powered electrically, to generate relative movement of the receptacle and a corresponding element to be moved selected amongst said members.

14. A catheter winder/unwinder according to claim 1, wherein each receptacle is in the form of a tank.

15. A system including *an exchangeable elongate tubular member, and* a catheter winder/unwinder comprising a receptacle adapted to receive [an] *said* elongate tubular member [for insertion into a duct of a patient and extending between a first end and a second end along a longitudinal direction];

the receptacle having an opening formed to allow said *elongate tubular* member to pass to the outside;

the winder/unwinder further comprising a drive mechanism adapted to apply to the *elongate tubular* member movement through said opening relative to said receptacle, said drive mechanism comprising:

an equipment mounted to move relative to the receptacle in a first degree of freedom, the equipment carrying the *elongate tubular* member; and an electric motoring device adapted to generate movement when powered electrically;

said electric motoring device being adapted to generate relative movement between the equipment and the receptacle in the first degree of freedom so as to generate relative movement of the *elongate tubular* member and of the receptacle in said first degree of freedom;

the *elongate tubular* member being mounted to move relative to the equipment in a second degree of freedom distinct from the first degree of freedom;

said electric motoring device being adapted to generate relative movement of the equipment and of the *elongate tubular* member in the second degree of freedom in order to generate relative movement of the *elongate tubular* member and of the receptacle in said second degree of freedom;

said electric motoring device comprising at least an electric motor, said electric motoring device comprising at least one movement transfer element connected to one of said electric motors to transmit said relative movement of the *elongate tubular* member and the equipment in the second degree of freedom from said electric motor;

the [installation] *system* comprising a permanent portion comprising said electric motors, and a utilized replaceable portion, distinct from said *elongate tubular* member, mounted removably relative to the permanent portion, the permanent portion and the replaceable portion in an assembled state together forming said winder/unwinder, the [installation] *system* having a plurality of replaceable replacement portions that are identical to the utilized replacement portion.

16. A system according to claim 15, wherein the replaceable portion comprises at least the receptacle.

17. A system according to claim 15, wherein the permanent portion includes the entire drive mechanism.

18. A system according to claim 15, wherein the drive mechanism includes an application portion in contact with the member and adapted, in the assembled state, to be connected to the movement transfer [mechanism] *element* to apply said relative movement of the member and of the receptacle in said second degree of freedom, and wherein the replaceable portion comprises at least said application portion.

19. A catheter winder/unwinder comprising a base adapted to receive [a tubular] *an elongate* member for inserting into a duct of a patient and extending between a first end and a second end along a longitudinal direction of the member, and a drive mechanism adapted to apply to said [tubular] *elongate* member at least movement along said longitudinal direction, said drive mechanism comprising:

*a rotation ring gear mounted on the base;*

*a translation ring gear mounted on the base;* a plate *having a top face* adapted to carry the *elongate* member and *an opposed bottom face, wherein the plate is* mounted to rotate relative to the base about said longitudinal direction *under actuation through the rotation ring gear*;

an application portion mounted to move on the plate, in contact with the *elongate* member, *wherein the application portion comprises at least one drive wheel*

*disposed on the top face of the plate, and at least one corresponding gear wheel disposed on the bottom face of the plate*;

a [wormscrew] *movement transfer system* mounted on the plate, *driven by the translation ring gear,* and adapted to drive said [application portion] *at least one drive wheels through said corresponding at least one gear wheel* so that said [application portion] *at least one drive wheels* moves on the plate so as to apply said movement to the [tubular] *elongate* member along the longitudinal direction; and an electric motoring device adapted to drive the [wormscrew] *movement transfer system through the translation ring gear*.

*20. A system according to claim 15, wherein the winder/unwinder comprises a plate having a bottom portion comprising drive shafts, and being part of the permanent portion, and having a top portion, part of the replaceable portion, and having wheels applying movement to the elongate tubular member and engaged by respective drive shafts.*

*21. A catheter winder/unwinder according to claim 19, wherein the movement transfer system comprises a wormscrew.*

*22. A catheter winder/unwinder according to claim 21, wherein the wormscrew is mounted to rotate on the plate in two bearings.*

*23. A catheter winder/unwinder according to claim 19, wherein the movement transfer system receives drive via an intermediate gear intermediate between the movement transfer system and the translation ring gear.*

*24. A catheter winder/unwinder according to claim 19, wherein the application portion comprises at least two drive wheels disposed on the top face of the plate, and at least two corresponding gear wheels disposed on the bottom face of the plate.*

*25. A catheter winder/unwinder according to claim 19, wherein the application portion comprises a non-motor driven wheel disposed on the top face, in contact with the elongate member.*

*26. A catheter winder/unwinder according to claim 25, further comprising an adjustment mechanism to adapt to catheters of different diameters.*

* * * * *